United States Patent [19]

Elson et al.

[11] Patent Number: 4,643,389
[45] Date of Patent: Feb. 17, 1987

[54] TUBING OCCLUSION CLIP

[75] Inventors: Edward E. Elson, Anaheim; Farley W. Bolwell, Newport Beach; Wayne E. Manska, Anaheim; Stanley G. Shoffner, Irvine, all of Calif.

[73] Assignee: American Hospital Supply Corporation, Evanston, Ill.

[21] Appl. No.: 686,989

[22] Filed: Dec. 27, 1984

[51] Int. Cl.⁴ ............................................. F16L 55/14
[52] U.S. Cl. ........................................ 251/10; 24/543
[58] Field of Search .................... 251/4–10; 24/542, 543, 518; 128/346

[56] References Cited

U.S. PATENT DOCUMENTS

| | | | |
|---|---|---|---|
| 2,722,932 | 11/1955 | Hickey | 128/214 |
| 2,915,062 | 12/1959 | Butler et al. | 128/214 |
| 2,941,778 | 6/1960 | Bujan | 251/9 |
| 3,135,259 | 6/1964 | Evans | 128/214 |
| 3,384,336 | 5/1968 | Pulman | 251/9 |
| 3,419,245 | 12/1968 | Scola | 251/10 |
| 3,759,483 | 9/1973 | Baxter | 251/7 |
| 3,822,052 | 7/1974 | Lange | 24/543 |
| 3,942,228 | 3/1976 | Buckman et al. | 251/4 |
| 4,053,135 | 10/1977 | Saliaris | 251/10 |
| 4,378,013 | 3/1983 | Lefevre | 251/7 |
| 4,429,852 | 2/1984 | Tersteegen et al. | 251/9 |
| 4,439,179 | 3/1984 | Lueders et al. | 251/9 |
| 4,453,295 | 6/1984 | Laszczower | 251/10 |

Primary Examiner—James C. Yeung
Attorney, Agent, or Firm—Gordon L. Peterson

[57] ABSTRACT

A tubing occlusion clip comprising a first wall portion, first and second arms joined to spaced regions of the first wall portion and a closing wall portion joined to the first arm and extendible to the second arm such that the arms cooperate with the wall portions to form a closed loop. The wall portions have openings, and a tube is coupled to the first wall portion and extends across the closed loop and through the opening of the closing wall portion. First and second clamping members are carried by the first and second arms, respectively, and they are adapted to have the tube extend therebetween. The arms are relatively movable toward each other to a clamping position in which the tube is clamped between the clamping members and relatively movable away from each other to a releasing position. Interlocking members are provided on the closing wall portion and the second arm for positively locking the closed loop against opening when the arms are in the releasing position.

9 Claims, 7 Drawing Figures

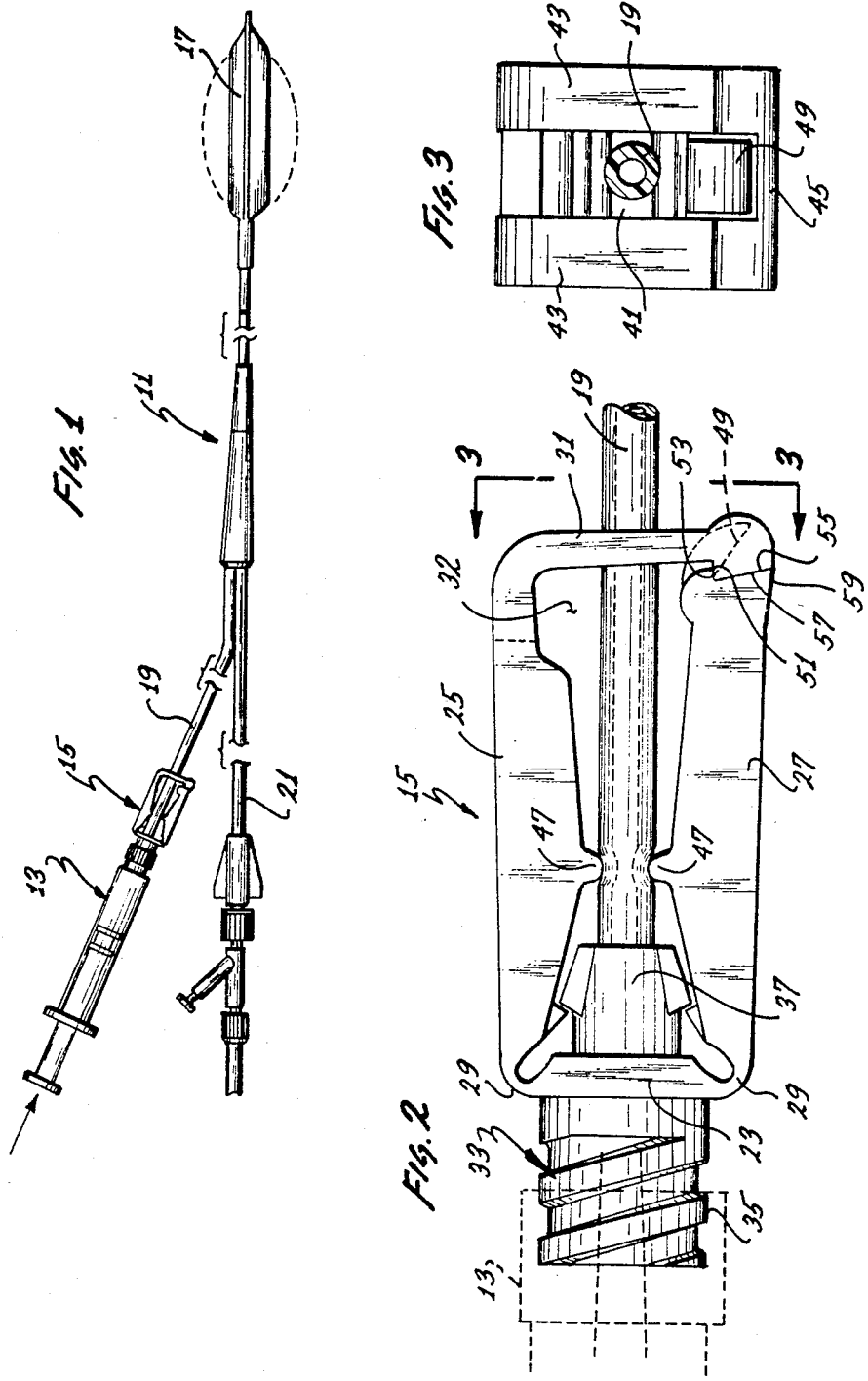

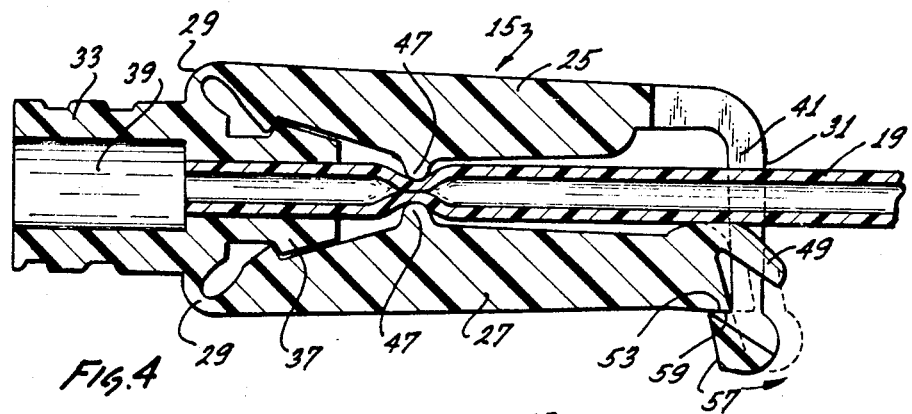
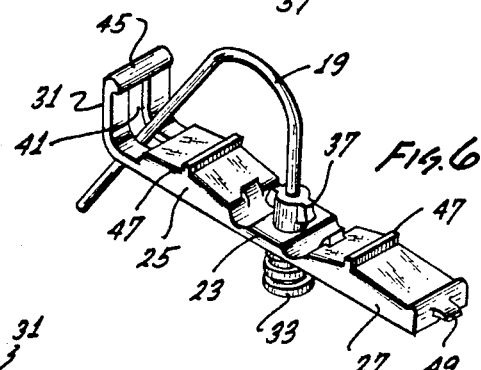
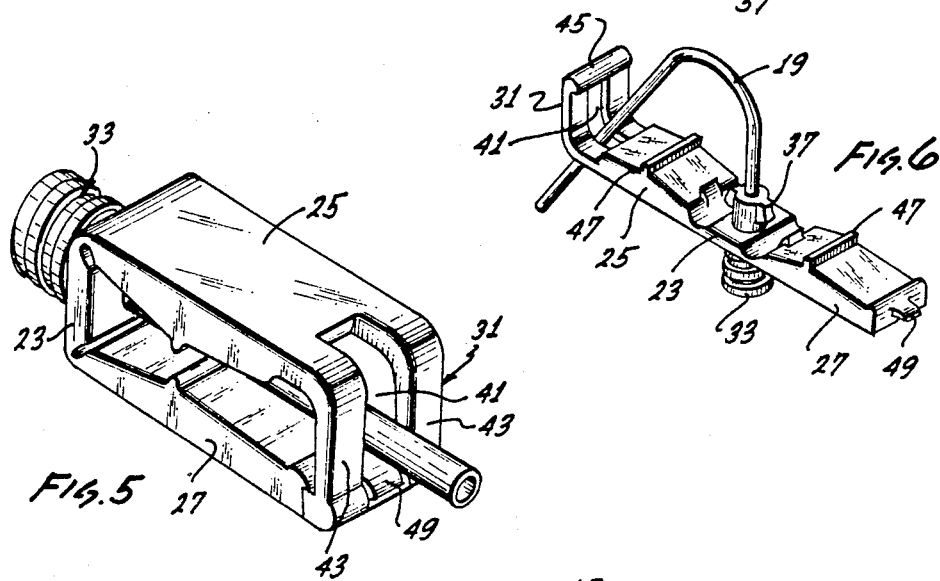
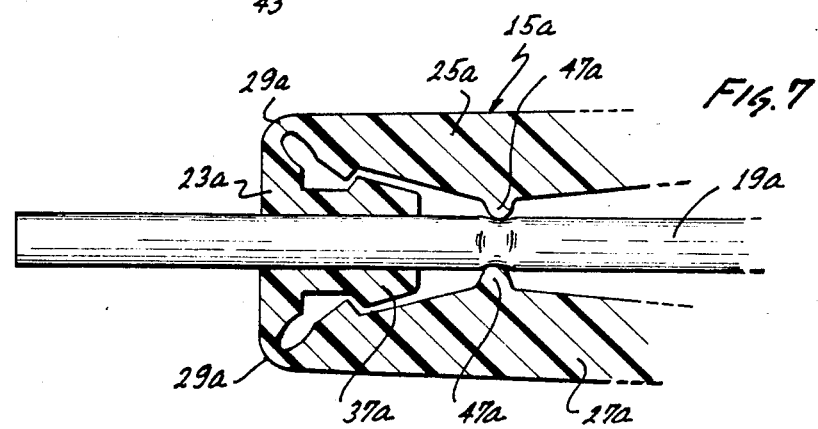

TUBING OCCLUSION CLIP

BACKGROUND OF THE INVENTION

Various medical procedures utilize resilient tubes to carry fluids, and on-off control of the flow of fluids through the tubes is obtained with a variety of devices, including stopcocks and clamps. For example, the balloon of a balloon catheter is commonly inflated with a syringe which forces inflation air through a resilient tube. When the balloon has been properly inflated, the tube is occluded with a clamp. Following use of the balloon to position the distal end of the catheter, the clamp is opened and the syringe is removed to deflate the balloon. In medical procedures such as this, it is important that the clamp be readily accessible to, and easily operable by, the physician.

Hickey U.S. Pat. No. 2,722,932 shows a tubing occlusion clamp which forms an open loop in the releasing or unclamped position. The open loop is subject to being caught on external members and permanently distorted. The distortion may prevent the clamp from completely pinching off the tube, or conversely, may cause the tube to be pinched so tightly that it is cut by the clamp. A similar prior art clamp which forms a closed loop in the unclamped position, but is not locked in the closed loop, is subject to the same problems.

SUMMARY OF THE INVENTION

This invention solves the problems discussed above by providing a tubing occlusion clip which is positively locked in a closed-loop configuration in both the clamping and releasing positions. The positive lock prevents the closed loop from being opened and distorted. Consequently, the likelihood of the tubing occlusion clip failing to completely pinch off the tube or cutting the tube is materially reduced.

The tubing occlusion clip of this invention is also easily operable with one hand and readily accessible. To assure that the tubing occlusion clip is always accessible to the physician, this invention preferably positively prevents the clip from sliding along the tube. This may be accomplished by molding the tube into the clip. Alternatively or in addition thereto, the clip may include a hub having means thereon for coupling the hub to another member, such as a syringe. This feature also eliminates the need for a separate hub.

In a preferred construction, the tubing occlusion clip includes a first wall portion, first and second arms joined to spaced regions of the first wall portion and being resiliently movable toward each other, and a closing wall portion joined to the first arm and extendible to the second arm so that the arms can cooperate with the wall portions to form a closed loop. First and second clamping members are carried by the first and second arms, respectively, and they are adapted to have a tube extend between them. The arms are relatively movable toward each other to a clamping position to clamp the tube and relatively movable away from each other to a releasing position in which the clamping members impose a lesser restriction to flow, which may be no restriction, through the tube. Means is provided for releasably retaining the arms in the clamping position.

The arms and the wall portions are positively locked in the closed-loop configuration by cooperating means on the closing wall portion and the second arm. This positive lock is effective when the arms are in either the releasing or clamping positions.

The cooperating means preferably includes interlocking means on the closing wall portion and the second arm. The interlocking means may include interlocking shoulders on the second arm and the closing wall portion. Alternatively, or in addition thereto, the cooperating means may include a portion of the closing wall portion and a tab on the second arm.

If a hub is to be provided, it is preferably carried by the first wall portion, and it projects outwardly of the closed loop. The hub includes means for coupling the hub to another member.

In order that the clip can cooperate with a tube, both of the wall portions preferably have openings therein so that the tube can extend through the clip. When the clip includes the hub, the opening in the first wall portion also preferably extends through the hub. Manufacture of the clip can be facilitated by integrally molding the clip from suitable plastic material. To further facilitate manufacture and to prevent movement of the clip along the tube, the tube can be molded into the opening in the first wall portion.

The invention, together with additional features and advantages thereof, may best be understood by reference to the following description taken in connection with the accompanying illustrative drawing.

BRIEF DESCRIPTION OF THE DRAWING

FIG. 1 is a side elevational view of a tubing occlusion clip constructed in accordance with the teachings of this invention and a balloon catheter and syringe.

FIG. 2 is a enlarged side elevational view of the tubing occlusion clip in the releasing or unclamped position, with a portion of the syringe shown in dashed lines.

FIG. 3 is an end view taken generally along line 3—3 of FIG. 2.

FIG. 4 is a longitudinal, sectional view through the tubing occlusion clip in the clamped position.

FIG. 5 is an isometric view of the tubing occlusion clip.

FIG. 6 is an isometric view of the tubing occlusion clip in the as-molded condition with the tube shown in a deflected position.

FIG. 7 is a fragmentary, sectional view similar to FIG. 4 illustrating another embodiment of the tubing occlusion clip.

DESCRIPTION OF THE PREFERRED EMBODIMENT

FIG. 1 shows a balloon catheter 11 coupled to a syringe 13 and having a tubing occlusion clip 15 releasably coupled to the syringe. The catheter 11, which may be of conventional construction, is illustrated for the purpose of showing one manner in which the clip 15 can be used. For example, the catheter 11 may be identical to the catheter shown in Ari et al application Ser. No. 666,873 filed on Oct. 31, 1984.

The catheter 11 includes a balloon 17 adjacent its distal end and a balloon inflation lumen, including a resilient, collapsible tube 19, for inflating the balloon. The catheter 11 may have additional lumens, including a tube 21, for infusion of fluids, monitoring of blood pressure, or other purposes.

The tube 19 is coupled to the syringe 13. Accordingly, the syringe 13 can be used in a conventional fashion to force air or other fluids through the tube 19 to the balloon 17 to inflate the balloon. The clip 15 would then be used to clamp, and subsequently release, the tube 19 as described below.

With reference to FIGS. 2-6, the clip 15, which is preferably integrally molded from polypropylene or other suitable plastic material, includes a first wall portion 23, first and second relatively rigid arms 25 and 27 integrally joined to spaced regions of the first wall portion 23 by hinges 29 of reduced thickness, and a closing wall portion 31 joined to the first arm 25 and extendible to the second arm 27 so that the arms cooperate with the wall portions to form a closed loop. The exterior surfaces of the wall portions 23 and 31 and of the arms 25 and 27 are generally flat, and the closed-loop configuration as viewed in FIG. 2 has a generally rectangular configuration, with a large opening or region 32 which is surrounded by the closed loop.

A hub 33 is molded integrally with the first wall portion 23 and projects outwardly of the closed loop. The hub 33 has external threads 35 for coupling it to the syringe 13. The hub 33 also has a tubular projection 37 projecting into the closed loop. An opening 39 (FIG. 4) extends through the hub 33 and the first wall portion 23, with the portion of the opening within the outwardly directed region of the hub 33 being radially enlarged.

An opening 41 (FIGS. 3-6) divides the closed wall portion 31 into a pair of spaced longitudinal straps 43 interconnected at their free ends by a member or web 45 of the wall portion 31. The web 45 is at the free end of the wall portion 31, and it extends across the opening 41. The opening 41 also extends into the arm 25.

The clip 15 is preferably molded in the open or flat condition of FIG. 6 in which the arms 25 and 27 are essentially coplanar with the first wall portion 23. The tube 19 is preferably molded into the opening 39 so that the tube is bonded to the projection 37. Of course, adhesive can be used on the tube 19 to accomplish the bonding, if necessary. In the folded or closed-loop position, the tube 19 extends from the opening 39 across the region 32 of the closed-loop configuration and out the opening 41 as shown in FIGS. 2, 4 and 5.

In order that the clip 15 can clamp and occlude the tube 19, first and second clamping members 47 are carried on the interior surfaces of the arms 25 and 27, respectively. The clamping members are directly opposite each other, and the tube 19 is adapted to extend between them.

The arms 25 and 27 are relatively movable toward each other to a clamping position (FIG. 4) in which the tube 19 is clamped between the clamping members 47 to completely block flow through the tube 19. The arms 25 and 27 are also relatively movable away from each other to a releasing position (FIG. 2) in which the clamping members 47 impose essentially no restriction to flow through the tube 19. The hinges 29 and the wall portion 31 are resilient, and resiliently oppose movement of the arms to the clamping position.

Cooperating means on the closing wall portion 31 and the second arm 27 positively locks the arms 25 and 27 and the wall portions 23 and 31 in the closed-loop configuration. A positive lock means that there is some structure or means holding the clip in the closed-loop configuration so that the closed loop cannot be opened without permanent deformation or breaking of the clip. In the illustrated embodiment, the cooperating means includes the web 45 and a tab 49 integral with, and projecting from the free end of, the arm 27. As shown in FIGS. 3 and 5, the tab 49 extends into the opening 41 and engages the web 45 in the releasing position to prevent movement of the arms 25 and 27 away from each other or opening of the closed loop.

In addition, in the illustrated embodiment of the invention, the cooperating means also includes interlocking shoulders 51 and 53 on the arm 27 and the wall portions 31, respectively. The shoulders 51 and 53 engage in the releasing position as shown in FIGS. 2 and 5 to positively lock the closed loop against opening.

To facilitate moving the arms 25 and 27 from the releasing position of FIG. 2 to the clamping position of FIG. 4, the arm 27 terminates in a cam 55, and the closing wall portion 31 has a cam follower 57 resiliently engaging the cam in the releasing position. The wall portion 31 is somewhat resilient, and this resilience holds the cam follower 57 against the cam 55. Accordingly, by pushing the arm 27 inwardly, the wall portion 31 is cammed in a direction away from the arm 27 until an outer surface 59 of the arm 27 is brought to about the same elevation as the shoulder 53 whereupon the wall portion 31 resiliently snaps inwardly to place the shoulder 53 beneath the outer surface 59 as shown in FIG. 4. This retains the arm 27 in this inward or clamping position in which the clamping members 47 tightly clamp the tube 19 to block the flow of fluid therethrough. It should be noted that the shoulders 51 and 53 are at the ends of the cam 55 and the cam follower 57, respectively, and that the shoulder 53 performs the dual functions of assisting to positively lock the clip 15 in the closed-loop configuration and releasably retaining the arms 25 and 27 in the clamped position.

To move the arms 25 and 27 back to the releasing position, the physician pushes with his thumb on the cam follower 57 to resiliently pivot the wall portion 31 in the direction of the arrow in FIG. 4 to the dashed line position to free the outer surface 59 from the shoulder 53 so that the resilience of the hinge 29 can move the arm 27 back to the releasing position of FIG. 2. Further movement of the arm 27 away from the arm 25 is prevented by the engagement of the shoulders 51 and 53 and the engagement of the tab 49 and the web 45.

The clip 15 can be used to clamp and release the tube 19 as may be desired for whatever medical procedure is to be carried out. For example, with the clip 15 in the releasing position of FIG. 2, the syringe 13 can be operated to inflate the balloon 17. Thereafter, the clip 15 can be moved to the clamping position of FIG. 4 to completely block the flow of air or other fluids through the tube 19. The balloon 17 is then used to carry portions of the catheter 11 to the desired location within the patient, and following this, the clip 15 is returned to the releasing position of FIG. 2, and the syringe 13 is unscrewed from the hub 33 to allow deflation of the balloon.

The clip 15 can be manually moved between the clamping and releasing positions with only one hand. Also, the clip 15 is mounted on the syringe, and the tube 19 is molded into the clip so that the clip will not slide along the tube.

FIG. 7 shows a tubing occlusion clip 15a which is identical to the tubing occlusion clip 15 in all respects not shown or described herein. Portions of the clip 15a corresponding to portions of the clip 15 are designated by corresponding reference numerals followed by the letter "a."

One difference between the clip 15a and the clip 15 is that the former has no hub portion extending outwardly of the closed loop so that the clip 15a is not attachable to an external member, such as the syringe 13. In addition, the tube 19a is not molded into the clip 15a. Accordingly, the clip 15a can be slid along the tube 19a.

Although an exemplary embodiment of the invention has been shown and described, many changes, modifications and substitutions may be made by one having ordinary skill in the art without necessarily departing from the spirit and scope of this invention.

We claim:

1. A tubing occlusion clip comprising:

an end wall portion;

first and second arms joined to spaced regions of the end wall portion and being resiliently movable toward each other;

a closing wall portion joined to said first arm and extendible to said second arm whereby said arms can cooperate with said wall portions to form a closed loop;

said arms being adapted to have a tube extend therebetween;

first and second clamping members carried by the first and second arms, respectively, and adapted to have the tube extend between the clamping members;

said arms being relatively movable toward each other to a clamping position in which the tube is clamped between said clamping members to at least restrict flow through the tube and relatively movable away from each other to a releasing position in which the clamping members impose a lesser restriction to flow through the tube;

said second arm terminating in a cam and having a shoulder and an outer surface at opposite ends of the cam;

said closing wall portion having a cam follower and a shoulder at the inner end of said cam follower;

said shoulders being in engagement in the releasing position whereby the arms are positively locked in the closed loop in the releasing position and said cam and said cam follower being in engagement in said releasing position whereby inward movement of the second arm moves the arms to the clamping position; and said outer surface engaging the shoulder of the closing wall portion in the clamping position to releasably retain the arms in the clamping position.

2. A tubing occlusion clip as defined in claim 1 wherein said wall portions have openings therein whereby the tube can extend from the opening in the end wall portion and across said closed loop and into the opening of the closing wall portion.

3. A tubing occlusion clip as defined in claim 2 wherein the closing wall portion includes a member extending across the opening thereof and a tab on the second arm is extendible into the opening of the closing wall portion and engageable with said member to at least assist in locking the closed loop against opening.

4. A tubing occlusion clip as defined in claim 2 including said tube and wherein said tube is coupled to the end wall portion at the opening in said end wall portion.

5. A tubing occlusion clip as defined in claim 4 including a hub carried by the end wall portion and having the opening in the end wall portion extending therethrough and the tube is molded into the opening in the end wall portion.

6. A tubing occlusion clip as defined in claim 5 wherein the closing wall portion includes a member extending across the opening thereof and a tab on the second arm is extendible into the opening of the closing wall portion and engageable with said member to at least assist in locking the closed loop against opening.

7. A tubing occlusion clip as defined in claim 1 wherein said tubing occlusion clip is integrally molded of plastic and said end wall portion and said arms are relatively rigid and integrally joined by resilient hinges.

8. A tubing occlusion clip as defined in claim 1 including a hub carried by the end wall portion, projecting outwardly of the closed loop, and having the opening in the end wall portion extending therethrough and mechanical means on the hub for coupling the hub to another member.

9. A tubing occlusion clip as defined in claim 1 wherein said closing wall portion terminates substantially flush with said outer surface of said second arm in said releasing position.

* * * * *